United States Patent [19]

Gilmore et al.

[11] Patent Number: 4,923,307

[45] Date of Patent: May 8, 1990

[54] DILATOMETER

[75] Inventors: James F. Gilmore, Rochester; Carl A. Lloyd, East Bloomfield, both of N.Y.

[73] Assignee: Eastman Kodak Company, Rochester, N.Y.

[21] Appl. No.: 301,210

[22] Filed: Jan. 24, 1989

[51] Int. Cl.⁵ .......................................... G01N 25/16
[52] U.S. Cl. ...................................... 374/55; 374/56; 336/30; 336/136
[58] Field of Search ............... 374/45, 55, 56; 73/763; 336/30, 136; 33/789

[56] References Cited

U.S. PATENT DOCUMENTS

| | | | |
|---|---|---|---|
| 2,627,062 | 1/1953 | Graham | 336/30 |
| 3,151,399 | 10/1964 | MacGeorge | 33/780 |
| 3,617,964 | 11/1971 | Bocksruker | 336/30 |
| 3,680,357 | 8/1972 | Clusener | 336/30 |
| 3,898,836 | 8/1975 | Clusener | 374/56 |
| 3,919,879 | 11/1975 | Betz | 374/56 |
| 4,521,119 | 6/1985 | Stepke et al. | 374/56 |
| 4,548,515 | 10/1985 | Cluesener | 374/56 |
| 4,762,424 | 8/1988 | Baricevac et al. | 374/56 |

FOREIGN PATENT DOCUMENTS 789716 12/1980 U.S.S.R. ................ 374/55

OTHER PUBLICATIONS

Dupont 940 Thermomechanical Analyzer, Pamphlet (1967).
Lloyd, L. T. "Recording Quartz Differential Dilatometer", Argonne National Laboratory, ANL-5372 (Jul. 1959).
Hyde, G. R. et al., "Improved Dilatometer", The Review of Scientific Instruments, vol. 36, No. 2, pp. 204–205 (Feb. 1965).
Loubser, P. J. et al., "An Apparatus for Determining the Coefficient for Thermal Expansion of Rocks Mortars and Concretes", Magazine of Concrete Research, vol. 24, No. 79, pp. 97–100 (Jun. 1972).

Primary Examiner—Allan N. Shoap
Assistant Examiner—Diego F. F. Gutierrez
Attorney, Agent, or Firm—Stephen C. Kaufman

[57] ABSTRACT

An improved dilatometer suitable for testing the coefficient of thermal expansion (CTE) of a workpiece. The workpiece having a CTE in the range of $-0.2 \times 10^{-6}$ inch/inch °F. to $0.2 \times 10^{-6}$ inch/inch/°F. The improvement includes a reference structure means for positioning and isolating the workpiece, and for maintaining an independent reference temperature, uninfluenced by a required workpiece temperature differential. The temperature independent reference structure means helps assure that measurements of expansions/contractions of the workpiece, as a function of temperature, are uniquely that of the workpiece, and not that of the reference structure means, or any other ambient temperature determinant. The improved dilatometer is particularly useful for determining the CTE of a workpiece having a relatively low value, e.g., a CTE less than $0.1 \times 10^{-6}$ inch/inch °F.

19 Claims, 2 Drawing Sheets

DILATOMETER

BACKGROUND OF THE INVENTION

1. Cross-Reference To A Related Application

This application is related to a copending and commonly assigned patent application Ser. No. 301,211, filed Jan. 24, 1989 to Gilmore et al, which is being filed contemporaneously with this application. The entire disclosure of this copending application is incorporated by reference herein.

2. Field of the Invention

This invention relates to an improved dilatometer suitable for determining the coefficient of thermal expansion of a workpiece.

3. Introduction to the Invention

The coefficient of thermal expansion (CTE) of a workpiece provides a measure of the deformations induced in the workpiece by a change in temperature. The CTE may be expressed by a well known equation (1):

$$CTE = \frac{\Delta L}{L \Delta T^\circ} \qquad (1)$$

where

L = length of a workpiece having a uniform thermal strain; and

ΔL = a linear deformation due to a change in temperature of ΔT°.

It is important to know the coefficient of thermal expansion, for example, when the workpiece is part of a statically indeterminate system. Here, expansions or contractions of the workpiece induced by a change of temperature, may be inhibited or entirely prevented in certain directions. This, in turn, may cause significant stresses in the system, which stresses may have to be investigated by way of the coefficient of thermal expansion, and subsequently accommodated by the system.

SUMMARY OF THE INVENTION

Our motivation for providing a novel dilatometer, suitable for determining the CTE of a workpiece, comes about in the following way. We are working with workpieces that comprise novel compositions; that may be utilized in systems of exceptional sensitivity and high performance; and which may be subjected to unusual thermal stresses. For example, the workpiece may comprise a critical component of an optics device that is mounted in a spacecraft. To the end of designing a workpiece to ensure a desired system performance, we determine its coefficient of thermal expansion. The CTE of our workpieces comprise an unusually wide range of values, e.g., from $0.2 \times 10^{-6}$ inch/inch °F. to $-0.2 \times 10.6$ inch/inch °F.

In general, dilatometer techniques for determining the CTE of a workpiece follow equation (1) above, which instructs one to determine ΔT and ΔL. Conventional dilatometer techniques for determining the CTE of a workpiece are set forth in the ASTM Standards. We have found that these conventional dilatometer techniques may be adequate when the required CTE is approximately $12 \times 10^{-6}$ inch/inch °F., or greater. Conventional dilatometer techniques may be acceptable, therefore, for determining the CTE of a "pure" workpiece, such as aluminum, which has a CTE of 12.9 inch/inch °F. On the other hand, we have found that conventional dilatometer techniques may not be suitable for the case where:

(1) the workpiece has a relatively much lower CTE than the last cited figure, say a CTE of less than $0.1 \times 10^{-6}$ inch/inch °F.; and/or (2) the workpiece comprises a composition that is not explicitly recited by the ASTM in its catalogue of CTE testing procedures. An example here is a workpiece comprising a composite e.g., a graphite/epoxy composite, or graphite/glass composite. It is noted that the CTE of the first composite may be as low as $0.03 \times 10^{-6}$ inch/inch °F., which is less than that of pure aluminum, and by approximately three orders of magnitude.

The deficiencies of the conventional techniques for determining the CTE of materials having a relatively low CTE value, and/or a novel composition, may include the introduction of systematic and random errors. Systematic errors result from the use of imperfect measuring instruments or methods of measurement not justified under the existing conditions. Random errors, on the other hand, result from limitations in the observer's skill or judgment and from influences, such as minute fluctuations in physical conditions, beyond the control of the observer.

As an example of systematic errors that may result from the use of imperfect measuring instruments, consider the case of a conventional dilatometer. Here, measuring the expansions/contractions of the workpiece as a function of temperature typically requires the employment of a position structure, for positioning the workpiece undergoing a CTE test. The position structure, moreover, may become part of the testing itself; that is, the position structure, as well as the workpiece, may expand/contract as a function of temperature. This dual action of movement between the position structure and/or the workpiece can lead to the systematic error of incorrectly imputing expansions/contractions of the position structure, to the workpiece. Some commercially available dilatometers, for example, the Harrop Series TD 720, TDA H1 and TDA H2 dilatometers available from Harrop Industries, Inc., address the indicated systematic error problem, by a control console that compensates or "backs out" the expansions/contractions due to the position structure. Implicitly, however, this dilatometer compensation control retains the underlying problem of incorporating the position structure into the testing itself, and it is unclear if the back outs are always adequate to redress the built in problem, especially when a CTE is in the range of less than $0.1 \times 10^{-6}$ inch/inch °F.

We have now discovered an improved dilatometer suitable for testing a coefficient of thermal expansion of a workpiece. In a first aspect, the present invention comprises an improved dilatometer comprising:

(a) a reference structure means connectable to the workpiece, for positioning and isolating the workpiece undergoing a CTE test, and capable of maintaining a temperature independent of the workpiece, so that a workpiece temperature differential ΔT induced by a CTE test is unique to the workpiece;

(b) means for producing and monitoring the temperature differential ΔT of the workpiece undergoing a CTE test;

(c) a transducer means connectible to the workpiece, for converting expansions/contractions of the workpiece undergoing the CTE test into a change of length ΔL parameter; and (d) means for connecting the workpiece to the reference structure means and the transducer means.

The improved dilatometer includes a temperature independent reference structure means that helps assure that measurements of expansions/contractions of the workpiece, as a function of temperature, are uniquely that of the workpiece, and not that of the reference structure means, or any other ambient temperature determinant. This can result in an improved signal to noise ratio, as compared, for example, to the previously discussed commercially available dilatometer. For the last case, it is indicated that the systematic error induced by the position structure can be as large, or larger, than a signal corresponding to a sought for CTE of the workpiece under test. In the present invention, in sharp contrast, this deficiency is obviated by why of the reference structure means as defined, thus realizing a high signal to noise ratio.

The present invention is particularly useful for testing the coefficient of thermal expansion of a workpiece having a relatively low value, for example, less than $0.1 \times 10^{-6}$ inch/inch °F., especially less than $0.03 \times 10^{-6}$ inch/inch °F. It is therefore advantageously employed for determining the CTE of composites like graphite/epoxy composites, that can have a CTE in the range from $0.2 \times 10^{-6}$ inch/inch °F. to $0.2 \times 10^{-6}$ inch/inch °F. Moreover, the dilatometer accuracy, which is the degree of conformity of a measured or calculated value to some recognized standard or specified value, is such that any systematic errors cannot vitiate the accuracy of a determined CTE. In particular, the improved dilatometer can determine a CTE within $\pm 1.7 \times 10^{-1}$ inch/inch °F. of a specified CTE.

In another aspect, the present invention provides a method for determining the coefficient of thermal expansion of a workpiece, which method comprises:

(a) providing a dilatometer comprising
  (1) a reference structure means connected to the workpiece, for positioning the workpiece; maintaining a temperature independent of the workpiece; and isolating the workpiece from ambient temperature determinants; and
  (2) a transducer means connected to the workpiece and the reference structure means, for converting transmitted expansions/contractions of the workpiece into a change of length parameter $\Delta L$; and (b) changing the temperature of the workpiece under isolation from an arbitrary and known state to a measurable isothermal state $\Delta T$, the changing temperature $\Delta T$ inducing expansions/contractions of the workpiece transmitted to the transducer means, for converting into the change in length parameter $\Delta L$.

BRIEF DESCRIPTION OF THE DRAWINGS

The invention is illustrated in the accompanying drawing, in which.

DETAILED DESCRIPTION OF THE INVENTION

Figure 1:
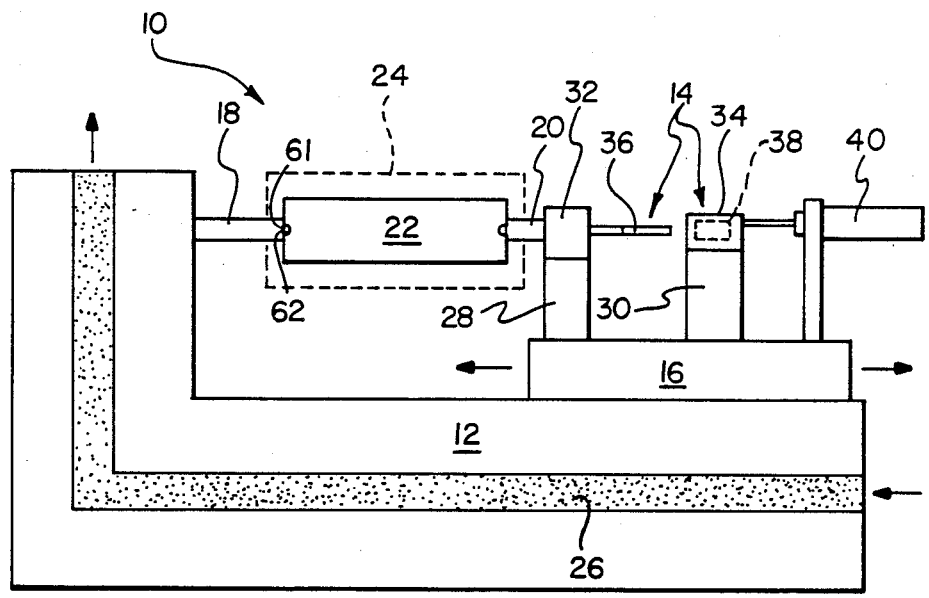
FIGS. 1 and 2A, B provide generalized diagrams of an improved dilatometer of the present invention.
Figure 1A:
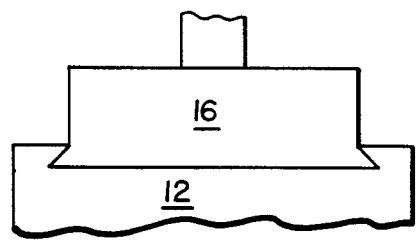

Attention is now directed to the drawing. FIG. 1 provides a generalized side-view diagram of an improved dilatometer of the present invention. The dilatometer 10 includes a reference structure means 12; a transducer means 14 connected to the reference structure means 12, by way of a slide assembly 16; a means 18, 20 for connecting a workpiece 22 to the reference structure means 12 and the transducer means 14, respectively; and a means 24 comprising a shroud assembly and a plurality of thermistors for producing and monitoring a temperature differential $\Delta T$ of the workpiece 22 undergoing a CTE test. These elements are now discussed in detail, one at a time.

The reference structure means 12 functions to position the workpiece 22, with respect to the transducer means 14; to isolate the workpiece 22 from ambient temperature determinants, other than the means 24 for producing the CTE test temperature differential $\Delta T$; and, to maintain a temperature independent of the workpiece 22. To this end, the reference structure means 12 preferably comprises a high thermal conductivity, low CTE material, such as INVAR and SUPER INVAR materials comprising a stainless steel alloy. ULE glass or fused silica may be used, but these are less satisfactory for the present purposes. The reference structure means 12, so composed, can maintain a temperature independent of the workpiece 22, preferably by way of a water cooled system 26, shown schematically in FIG. 1. The water cooled system 26 provides a controlled flow of water through the reference structure means 12, to maintain a constant reference temperature, e.g., 68° F. A conventional water cooled system can be used for this purpose. Alternatives to the preferred water cooled system 26 include a water or oil bath immersion system (not shown).

The reference structure means 12 shown in FIG. 1 has a preferred L shaped geometry, although other designs, including a C clamp geometry, can be viable alternatives. The reference structure means 12 includes a protruding portion 18, that already has been identified as the means for connecting the workpiece 22 to the reference structure 12. The portion 18, like the complementary means 20, preferably comprises a very low thermal conductivity, very low CTE material, to thereby provide a temperature gradient isolation transition function between the reference structure means 12 (or the transducer means 14) and the workpiece 22. A suitable portion 18 and means 20 preferably comprises a ULE composition, shaped as a post, as shown, with a spherical button 61 that registers in a spherical dimple 62 on one end of the workpiece 22.

The reference structure means 12 is connected on the base part of its L shape, to the slide assembly 16. The slide assembly 16 is an intermediary between the reference structure means 12 and the transducer means 14. The slide assembly 16 preferably is a dove tail assembly which helps position and lock the transducer means 14 to the workpiece 22. The movement of the dove tailed slide assembly 16, with respect to the reference structure means 12, is indicated in FIG. 1 by an arrow. The slide assembly 16 preferably comprises a high thermal conductivity, low CTE material, such as INVAR material. Extending from the slide assembly 16 are a core flexure 28 and a coil flexure 30. (The terms "core" and "coil" derive from components of the transducer means 14, as explained in detail below). The core flexure 28 and the coil flexure 30 operate in tandem, and provide a solution to a problem we have identified; namely, that a workpiece undergoing Pansions/contractions during testing, may shift or tilt out of alignment with the transducer means 14. The flexures 28, 30, however, can accommodate such expansions/contractions so that, for example, a desired parallelism between the transducer means 14 and the workpiece 22 can be maintained. The core flexure 28 and coil flexure 30 terminate in mounting blocks 32, 34 respectively. The mounting block 32 holds a transducer core, and has a temperature isolation capability, that cooperates with the means 20, to isolate the workpiece 22 from the transducer means 14. The mounting block 34, in turn, holds or encapsulates a transducer coil. The blocks 32, 34 preferably comprise a low thermal conductivity, low CTE, non ferric material, including, for example, phenolic ULE or fused silica materials.

As indicated above, the transducer means 14 is connectible to the workpiece 22, by way of the means 20, and is connected to the slide assembly 16 by way of the flexures 28, 30. The transducer means 14 functions to convert expansions/contractions of the workpiece 22 undergoing a CTE test, into a change of length or displacement parameter $\Delta L$. To this end, the transducer means 14 preferably comprises a linear variable differential transformer (LVDT). The LVDT comprises a transformer probe rod or core 36, connected to the workpiece 22 by way of the means 20 and mounting block 32, which probe rod 36, in response to expansions/contractions of the workpiece 22, transmits the displacement $\Delta L$ to an electromagnetic coil 38 of the LVDT. This last action, in turn, converts the displacement $\Delta L$ into a proportional voltage signal, which can be routinely converted into the parameter $\Delta L$ of equation (1) supra. A precision micrometer 40, connected to the coil mounting block 34 and the slide assembly 16, is preferably employed to "zero". the LVDT. A conventional LVDT and associated micrometer may be employed for this purpose.

Figure 2A:
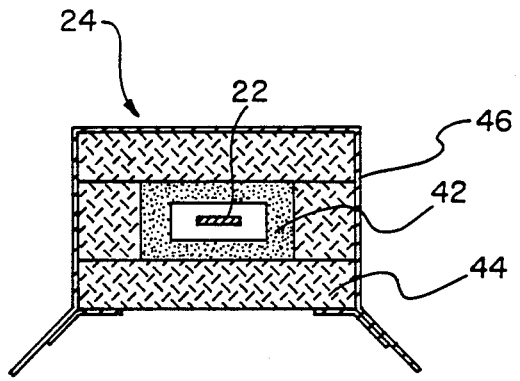
Figure 2B:
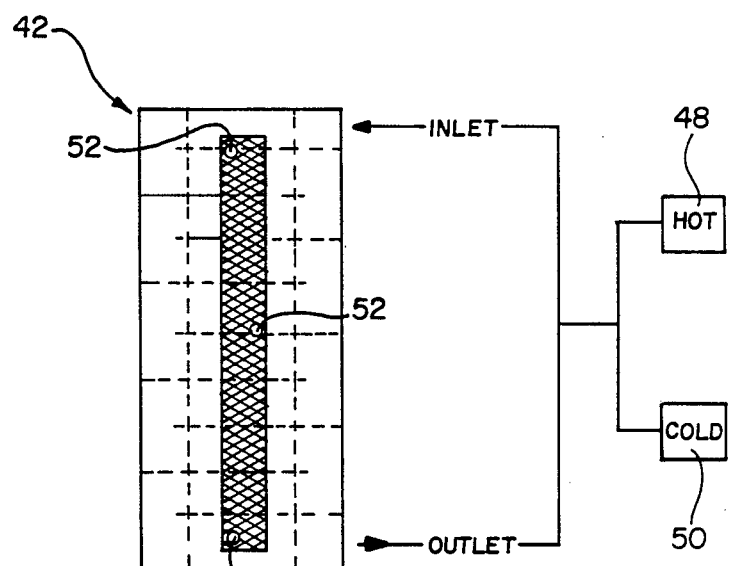

The workpiece 22 expands/contracts a distance $\Delta L$ in response to a temperature differential $\Delta T$. This temperature differential $\Delta T$ is preferably effected by way of a shroud assembly 24, shown in FIGS. 2A, B, which encloses the workpiece 22. FIG. 2A is a top-view of the shroud assembly, and FIG. 2B is a detail of FIG. 2A. The shroud assembly 24 functions to provide an optimum heat exchange capability to the workpiece 22, and to this end, preferably comprises a two walled, high thermal conductivity baffle structure 42, comprising aluminum to help ensure a uniform workpiece temperature and bafffle 60. Insulating material 44, preferably comprising a styrofoam composition, is also employed to ensure the uniform workpiece temperature. The insulating material 44 is secured by a shroud mounting bracket 46.

The shroud assembly 24, as shown in FIG. 2B, heats and cools the workpiece 22, via external hot and cold water reservoirs 48, 50, to best effect the temperature differential $\Delta T$. The actual measurement of the workpiece 22 temperature differential $\Delta T$ is preferably accomplished by way of a plurality of thermistors 52, directly attached to the workpiece 22.

What is claimed is:

1. An improved dilatometer suitable for determining the coefficient of thermal expansion (CTE) of a workpiece, said workpiece having a dimension bounded by two points and having a CTE in the range of $-0.2 \times 10^{-6}$ inch/inch °F. to $+0.2 \times 10^{-6}$ inch/inch °F., said dilatometer comprising:
   means, including an insulated enclosure, for imparting a controlled temperature differential $\Delta T$ to the workpiece when the workpiece is received in said enclosure;
   a reference structure comprising a high thermal conductivity, low CTE material; means for maintaining said reference structure at a constant uniform reference temperature;
   a transducer, wholly located outside of said insulated enclosure and including a movable member, and means for converting movement of said movable member into a change in length parameter $\Delta L$; means mounting said transducer to said reference structure; and
   means, including oppositely directed first and second members each located substantially outside of said enclosure and each comprising a low thermal conductivity, very low CTE material, for respectively connecting one point of the workpiece to said reference structure and the other point of the workpiece to said movable member, so that changes in the dimension of the workpiece caused by said temperature differential $\Delta T$ will be converted into said change in length parameter $\Delta L$.

2. An improved dilatometer as in claim 1, further comprising thermistor means for monitoring said temperature differential $\Delta T$.

3. An improved dilatometer as in claim 1, wherein said reference structure temperature maintaining means comprises a water cooling system for circulating water through said structure.

4. An improved dilatometer as in claim 1, wherein said transducer mounting means comprises a slide assembly.

5. An improved dilatometer as in claim 4, wherein said slide assembly comprises a dove-tailed connection between said transducer and said reference structure.

6. An improved dilatometer as in claim 1, wherein said transducer means further comprises a coil and a movable core; and wherein said means for connecting said other point to said movable member comprises means connecting said other point to said core.

7. An improved dilatometer as in claim 6, wherein said transducer means further comprises first and second flexure members respectively supporting said core and coil relative to said reference structure.

8. An improved dilatometer as in claim 1, wherein said means for imparting a temperature differential is a shroud assembly comprising a two-walled high conductivity baffle structure, a shroud mounting bracket, and insulating material secured by said shroud bracket about said baffle structure.

9. An improved dilatometer as in claim 8, wherein said temperature differential imparting means further comprises water heating and cooling reservoirs for heating and cooling said baffle structure.

10. An improved dilatometer as in claim 1, for determining the CTE of an elongated workpiece having opposing ends with spherical dimples, wherein said first and second members each comprises a post member with a free end in the form of a spherical button for registering with a respective one of the spherical dimples of the workpiece.

11. An improved dilatometer as in claim 1, wherein said transducer mounting means comprises a high thermal conductivity, low CTE material.

12. An improved dilatometer as in claim 11, wherein said CTE's of said first and second members are of the order of magnitude of ULE titanium silicate composition and the CTE's of said reference structure and said transducer mounting means are of the order of magnitude of INVAR stainless steel alloy.

13. An improved dilatometer as in claim 11 wherein said insulated enclosure has first and second ends, said reference structure includes a first portion proximate said first end and a second portion proximate said second end, said transducer mounting means comprises means mounting said transducer to said reference structure at said first portion; and said workpiece connecting means comprises means connecting said one point of said workpiece to said reference structure at said second portion.

14. An improved dilatometer suitable for determining the coefficient of thermal expansion (CTE) of an elongated workpiece, said workpiece having a length, opposite ends, and a CTE in the range of $-0.2 \times 10^{-6}$ inch/inch °F. to $+0.2 \times 10^{-6}$ inch/inch °F., said dilatometer comprising:

means, comprising an insulated shroud assembly, for imparting a controlled temperature differential $\Delta T$ to the workpiece when the workpiece is received within the shroud assembly;

means, located within the shroud assembly, for monitoring said temperature differential $\Delta T$;

a reference structure comprising a high thermal conductivity, low CTE material;

means for maintaining said reference structure at a constant uniform reference temperature;

a transducer, wholly located outside of said insulated enclosure, and comprising a linear variable voltage differential transformer having a coil and a core, one of said coil and core being movable, and said transducer further comprising means for converting relative movement of said movable one of said coil and core into a change in length parameter $\Delta L$;

a slide assembly, comprising a high thermal conductivity, low CTE material, mounting said transducer means to said reference structure;

means, including first and second oppositely directed posts each located substantially outside of said shroud assembly and each comprising a low thermal conductivity, very low CTE material, for respectively connecting one end of the workpiece to said reference structure and the other end of the workpiece to said one of said coil and core, so that changes in the length of the workpiece caused by said temperature differential $\Delta T$ will be converted into said change in length parameter $\Delta L$.

15. An improved dilatometer as in claim 14, wherein transducer further comprises first and second flexures connected to said slide assembly, and first and second blocks of low thermal conductivity, very low CTE, non-ferric material respectively monitoring said coil and core to said first and second flexures.

16. A method for determining the coefficient of thermal expansion (CTE) of a workpiece, said workpiece having a dimension bounded by two points and having a CTE in the range of $-0.2 \times 10^{-6}$ inch/inch °F. to $+0.2 \times 10^{-6}$ inch/inch °F., said method comprising:

placing the workpiece within an insulated enclosure;

connecting one point of the workpiece by means of a first member to a reference structure of high thermal conductivity, low CTE material and connecting the other point of the workpiece by means of an oppositely directed second member to a movable member of a transducer assembly which converts movement of said movable member into a change in length parameter $\Delta L$; with said first and second members being of low thermal conductivity, very low CTE materials and being located substantially outside of said enclosure, and said transducer assembly being located wholly outside of said enclosure;

maintaining the reference structure at a constant uniform reference temperature;

imparting a controlled temperature differential $\Delta T$ to the workpiece received in said enclosure;

monitoring the temperature differential $\Delta T$; and determining the coefficient of thermal expansion of the workpiece from the parameter $\Delta L$ and the monitored temperature differential $\Delta T$.

17. A method as in claim 16, wherein the transducer assembly comprises a variable voltage differential transformer mounted to the reference structure by means of a slide assembly having high thermal conductivity and low CTE, the second member connects said other point of the workpiece to said transducer assembly at a core of said transformer, and said core is mounted for movement relative to said slide assembly so that changes in the dimension of the workpiece caused by said temperature differential $\Delta T$ will be converted into said change in length parameter $\Delta L$.

18. A method as in claim 17, wherein the CTE's of said first and second members are of at least one order of magnitude less than the CTE's of said reference structure and said slide assembly.

19. A method as in claim 18, wherein the workpiece has a length and opposite ends with spherical dimples, wherein said first and second members are posts with spherical button tips, and wherein said connecting step comprises respectively connecting said button tips to said spherical dimples.

* * * * *

UNITED STATES PATENT AND TRADEMARK OFFICE
CERTIFICATE OF CORRECTION

PATENT NO. : 4,923,307
DATED : May 8, 1990
INVENTOR(S) : James F. Gilmore et al.

It is certified that error appears in the above-identified patent and that said Letters Patent is hereby corrected as shown below:

Col. 1, line 56      delete "10.6" and substitute therefor $--10^{-6}--$;

Col. 3, line 32      delete "$10^{-1}$" and substitute therefor $--10^{-8}--$;

Col. 4, line 62      delete "Pansions" and substitute therefor --expansions--.

Signed and Sealed this

Third Day of September, 1991

*Attest:*

HARRY F. MANBECK, JR.

*Attesting Officer*      *Commissioner of Patents and Trademarks*